United States Patent [19]

Cardin et al.

[11] Patent Number: 5,359,131
[45] Date of Patent: Oct. 25, 1994

[54] SULFONIC ACID DERIVATIVES IN THE TREATMENT OF VIRAL DISEASES

[75] Inventors: Alan D. Cardin; Norton P. Peet, both of Cincinnati; Nelsen L. Lentz, West Chester, all of Ohio

[73] Assignee: Merrell Dow Pharmaceuticals Inc., Cincinnati, Ohio

[21] Appl. No.: 106,311

[22] Filed: Aug. 13, 1993

Related U.S. Application Data

[63] Continuation of Ser. No. 838,639, Feb. 20, 1992, abandoned.

[51] Int. Cl.$^5$ ............................................. C07C 229/00
[52] U.S. Cl. ..................................... 562/51; 562/48; 562/53; 562/55; 562/56; 562/57
[58] Field of Search ....................... 562/48, 51, 53, 55, 562/56, 57

[56] References Cited

U.S. PATENT DOCUMENTS

| | | | |
|---|---|---|---|
| 2,676,982 | 6/1951 | Freyermuth et al. | 562/48 |
| 4,107,202 | 8/1978 | Conrow et al. | 424/315 |
| 4,328,244 | 5/1982 | Daniel et al. | |
| 4,349,568 | 9/1982 | Markley et al. | |
| 4,435,394 | 3/1984 | Ogata et al. | |

FOREIGN PATENT DOCUMENTS

| | | |
|---|---|---|
| A660945 | 7/1965 | Belgium . |
| 0221021 | 5/1987 | European Pat. Off. . |
| 0467185 | 1/1992 | European Pat. Off. . |
| 0498095 | 8/1992 | European Pat. Off. . |
| 3528992 | 2/1987 | Fed. Rep. of Germany . |
| 3600046 | 7/1987 | Fed. Rep. of Germany . |
| 2179347 | 3/1987 | United Kingdom . |
| 8800828 | 2/1988 | World Int. Prop. O. . |

OTHER PUBLICATIONS

Chemical Abstracts, vol. 81, No. 8, 26 Aug. 1974, Columbus, Ohio US; Abstract No. 38919s, L. A. Holt et al, p. 85; col. 2.
Chemical Abstracts, vol. 76, No. 12, 20 Mar. 1972, Columbus, Ohio US; Abstract No. 60909g, Y. Yamashita, p. 66; col. 2.
Chemical Abstracts, vol. 74, No. 22, 31 May 1971, Columbus, Ohio US; Abstract No. 11319j, Y. Yamashita, p. 51; col. 1.
Chemical Abstracts, vol. 98, No. 17, 25 Apr. 1983, Columbus, Ohio US; Abstract No. 141183X, R. R. Mayrand et al., p. 391; col. 2.
Chemical Abstracts, vol. 112, No. 3, 15 Jan. 1990, Columbus, Ohio US; Abstract No. 18775x, T. Sugihara, p. 286; col. 2.
Chemical Abstracts, vol. 85, No. 5, Aug. 1976, Columbus, Ohio US; Abstract No. 32589x, I. V. Aleksandrov et al., p. 359; col. 2.
Chemical Abstracts, vol. 84, No. 11, 15 Mar. 1976, Columbus, Ohio US; Abstract No. 69813u, L. Zaki et al., p. 73; col. 2.
Chemical Abstracts, vol. 82, No. 15, 14 Apr. 1975, Columbus, Ohio US; Abstract No. 93787t, D. Lorke., p. 99; col. 2.
Chemical Abstracts, vol. 78, No. 6, 12 Feb. 1973, Columbus, Ohio US; Abstract No. 31400v, Y. Yamashita, p. 80; col. 1.
Chemical Abstracts, vol. 77, No. 2, 10 Jul. 1972, Columbus, Ohio US; Abstract No. 7276t, E. Killman et al, p. 116; col. 2.
Chemical Abstracts, vol. 53, No. 3, 10 Feb. 1959, Columbus, Ohio US; Abstract No. i, D. Almparsky et al,; col. 2629.
Chemical Abstracts, vol. 78, No. 16, 23 Apr. 1973, Columbus, Ohio US; Abstract No. 98989n, T. Ohkubo, et al; p. 73 col. 1.
Chemical Abstracts, vol. 73, No. 5, 3 Aug. 1970, Columbus, Ohio US; Abstract No. 25375w, A. Y. Zheltov et al,; p. 359 col. 1.

(List continued on next page.)

*Primary Examiner*—Marianne M. Cintins
*Assistant Examiner*—Keith MacMillan
*Attorney, Agent, or Firm*—William R. Boudreaux

[57] ABSTRACT

Sulfonic acid stilbenes are disclosed which block the infection of cells by HSV, HIV and CMV.

11 Claims, No Drawings

OTHER PUBLICATIONS

Chemical Abstracts, vol. 64, No. 3, 31 Jan. 1966, Columbus, Ohio US; Abstract No. h, J. Brunken et al,; col. 2908.

Beigel et al.,. Exp. Cell res. 126, pp. 448–453 (1980).

Cabantchik et al, J. Membrane Biol. 10, pp. 311–330, (1972).

Rosoff et al., J. Med. Chem. vol. 263, No. 36, pp. 19535–19540 (1988).

Kawasaki et al., J. Biochem 106, pp. 401–405 (1989).

Cardin et ., "Stilbene Disulfoinic Acids. CD4 Antagonists that Block Human Immunodeficiency Virus Type-1 Growth at Multiple Stages of the Viral Life Cycle".

Huang et al., Molecular Pharmacology, 37, pp. 304–310 (1989).

Hofferek et al., Chemical Abstracts vol. 114; 180333q (1990).

Komp et al., Chemical Abstracts vol. 110; 33727k (1989).

SULFONIC ACID DERIVATIVES IN THE TREATMENT OF VIRAL DISEASES

This is a continuation of application Ser. No. 07/838,639, filed Feb. 20, 1992, now abandoned.

BACKGROUND OF THE INVENTION

A great deal of research is currently underway to develop treatments and cures for viral infections in humans and in animals. Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including Kaposi's sarcoma and Pneumocystis carninii pneumonia. No cure for AIDS is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then incorporated into the chromasomal DNA of the host cell making possible viral replication by transcription of this integrated DNA and translation of viral messenger RNA into proteins; assembly of new vital RNA into a protein core and release from the cell results in the formation of infectious virus progeny.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

The envelope protein of HIV is a 160 kDa glycoprotein. The protein is cleaved by a protease to give a 120 kDa external protein, gp 120, and a transmembrane glycoprotein, gp 41. The gp 120 protein contains the amino acid sequence that recognizes the receptor on CD4-positive human T-helper cells. Applicants have discovered that a class of sulfonated stilbenes that bear sulfonic acid groups are active against HIV. Herpes Simplex Viruses (HSV) I and II as well cytomegalovirus (CMV) have functionally related glycoprotein coatings and infections caused by these viruses can also be diminished or eliminated by the use of the sulfonated stilbenes of this invention.

SUMMARY OF THE INVENTION

The present invention provides novel compounds of Formula (I)

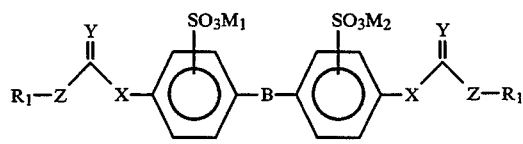

wherein

B is —CH=CH— (cis or trans), —CH$_2$CH$_2$— or a bond;

X is NH or Oxygen;

Y is Oxygen or Sulfur;

Z is NH, CH$_2$, Oxygen or Sulfur;

R$_1$ is hydrogen, C$_1$-C$_4$ alkyl, —CH$_2$—Ar, or —Ar wherein Ar is a phenyl or naphthyl group, the phenyl or naphthyl groups optionally substituted by a C$_1$-C$_4$ alkyl or SO$_3$M$_3$ group; and M$_1$, M$_2$, and M$_3$ are each independently a hydrogen or a pharmaceutically acceptable cation.

DETAILED DESCRIPTION OF THE INVENTION

As used herein, the term "C$_1$-C$_4$alkyl" refers to a saturated straight or branched chain hydrocarbyl radical of one to four carbon atoms and includes methyl, ethyl, propyl, isopropyl, n-butyl, isobutyl, tertiary-butyl and the like. The term "Ar" means a phenyl, benzyl, naphthyl ($\alpha$ and $\beta$), and methylnaphthyl ($\alpha$ and $\beta$) wherein the phenyl, benzyl, naphtyl, and methylnapthyl groups can be substituted on any available aromatic carbon atom with an alkyl group or a sulphonyl group. Specifically included within the scope of the term "Ar" are phenyl, benzyl, naphthyl ($\alpha$ and $\beta$), sodium p-phenylsulfonate, sodium m-phenylsulfonate, p-tolyl, m-tolyl, and sodium 4-naphthylsulfonate. The pharmaceutically acceptable cations, M$_1$, M$_2$, and M$_3$ are those cations that are not substantially toxic at the dosage administered to achieve the desired effect and do not independently possess significant pharmacological activity. Illustratively, these salts include those of alkali metals, for example, sodium and potassium; alkaline earth metals, such as calcium and magnesium; light metals of group IIIA including aluminum; and organic primary, secondary and tertiary amines, for example, trialkylamines, including triethylamine, procaine, dibenzylamine, N,N'-dibenzylethylenediamine, dihydroabiethylamine, N-(lower)alkylpiperidine, and any other suitable amine. Sodium salts are preferred.

The compounds of Formula I wherein X is NH, Y is oxygen or sulfur and Z is methylene, oxygen or NH, can be prepared by utilizing procedures and techniques well known and appreciated by one of ordinary skill in the art. A general synthetic scheme for preparing these compounds is described in Scheme I wherein all the substituents, unless otherwise indicated, are previously defined.

Scheme I

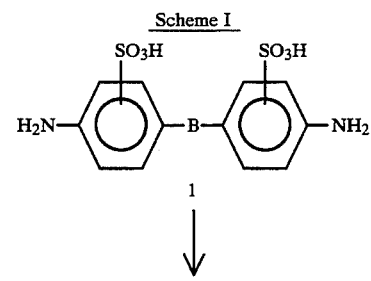

-continued
Scheme I

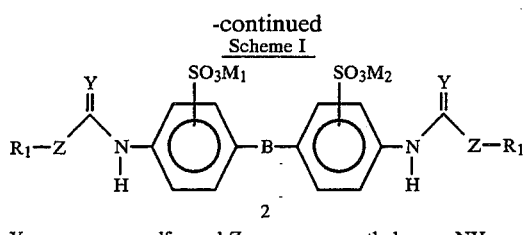

Y = oxygen or sulfur and Z = oxygen, methylene or NH

The compounds of Formula I wherein Y and Z are oxygen can be prepared by reacting the appropriate diamino compound of structure 1 for example, with two equivalents of 2-(tert-butoxycarbonyloxyimino)-2-phenylacetonitrile in a suitable aqueous solvent, such as 50% aqueous dioxane, with triethylamine, present at room temperature to provide the desired dicarbamate as defined by structure 2.

The compounds of Formula I wherein Y is oxygen and Z is methylene can be prepared by reacting the appropriate diamino compound of structure 1 for example, with an excess of the appropriately substituted anhydride [($R_1CO)_2O$] with heat to provide the desired diamide as defined by structure 2.

The compounds of Formula I wherein Y is oxygen and Z is NH can be prepared by reacting the appropriate diamino compound of structure 1 for example, with 2 equivalents of the appropriately substituted isocyanate ($R_1NCO$) in a dry organic solvent such as pyridine to provide the desired diurea as defined by structure 2.

The compounds of Formula I wherein Y is sulfur and Z is NH can be prepared by reacting the appropriate diamino compound of structure 1 for example, with 2 equivalents of the appropriately substituted isothiocyanate ($R_1NCS$) in a dry organic solvent such as pyridine to provide the desired dithiourea as defined by structure 2.

The compounds of Formula I wherein X is NH, Y is oxygen or sulfur and Z is NH, methylene, oxygen or sulfur, can be prepared by utilizing procedures and techniques well known and appreciated by one of ordinary skill in the art. A general synthetic scheme for preparing these compounds is described in Scheme II wherein all the substituents, unless otherwise indicated, are previously defined.

Scheme II

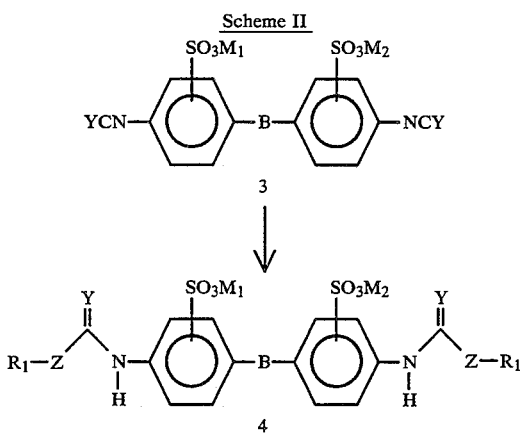

Y = Oxygen or Sulfur and Z = NH, $CH_2$, Oxygen or Sulfur

The compounds of Formula I wherein Y is oxygen and Z is NH can be prepared by reacting the appropriate diisocyanate of structure 3 with two equivalents of an appropriately substituted amino compound ($R_1NH_2$) in a previously dried organic solvent such as pyridine at room temperature to provide the desired diurea as defined by structure 4.

The compounds of Formula I wherein Y is oxygen and Z is sulfur can be prepared by reacting the appropriate diisocyanate of structure 3 with two equivalents of an appropriately substituted mercaptan ($R_1SH$) in a previously dried organic solvent such as pyridine at room temperature to provide the compound defined by structure 4.

The compounds of Formula I wherein Y is oxygen and Z is oxygen can be prepared by reacting the appropriate diisocyanate of structure 3 with two equivalents of an appropriately substituted alcohol ($R_1OH$) in a previously dried organic solvent such as pyridine at room temperature to provide the desired dicarbamate as defined by structure 4.

The compounds of Formula I wherein Y is sulfur and Z is NH can be prepared by reacting the appropriate diisothiocyanate of structure 3 with two equivalents of an appropriately substituted amino compound ($R_1NH_2$) in a wet solvent such as 50% aqueous pyridine at room temperature to provide the desired dithiourea as defined by structure 4.

The compounds of Formula I wherein Y is sulfur and Z is a methylene can be prepared by reacting the appropriate diisothiocyanate of structure 3 with two equivalents of an alkyl lithium ($R_1Li$) in a previously dried organic solvent such as tetrahydrofuran with two equivalents of hexamethylphosphoramide at −75° C. to provide the desired dithioamide as defined by structure 4.

The compounds of Formula I wherin Y is sulfur and Z is sulfur can be prepared by reacting the appropriate diisothiocyante of structure 3 with two equivalents of an appropriately substituted mercaptan ($R_1SH$) in a wet solvent such as 50% aqueous pyridine at room temperture to provide the compound defined by structure 4.

The compounds of Formula I wherin Y is sulfur and Z is an oxygen can be prepared by reacting the appropriate diisothiocyanate of structure 3 with two equivalents of an appropriately substituted alcohol ($R_1OH$) in a previously dried organic solvent such as pyridine to provide the desired compound defined by structure 4.

The compounds of Formula I wherin X is oxygen, Y is oxygen or sulfur and Z is NH, methylene, oxygen or sulfur, can be prepared by utilizing procedures and techniques well known and appreciated by one of ordinary skill in the art. A general synthetic scheme for preparing these compounds is described in Scheme III wherein all the substituents, unless otherwise indicated, are previously defined.

Scheme III

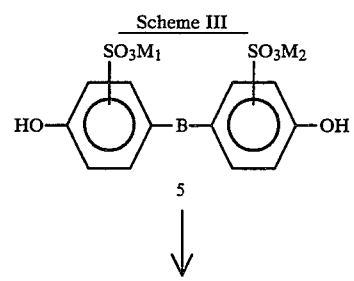

-continued
Scheme III

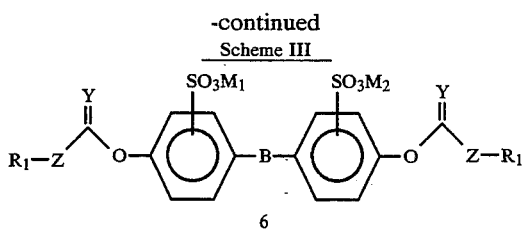

Y = Oxygen or Sulfur and Z = NH, CH$_2$, Oxygen or Sulfur

The compounds of Formula I wherein Y is oxygen and Z is NH can be prepared by reacting the appropriate diphenol of structure 5 with two equivalents of an appropriately substituted isocyanate (R$_1$NCO) in a previously dried organic solvent such as pyridine with minimal heating to provide the desired dicarbamate as defined by structure 6.

The compounds of Formula I wherein Y is oxygen and Z is methylene can be prepared by reacting the appropriate diphenol of structure 5 with two equivalents of an appropriately substituted acid chloride (R$_1$COCl) in a previously dried basic organic solvent such as pyridine, at room temperature to provide the desired diester as defined by structure 6.

The compounds of Formula I wherein Y is oxygen and Z is oxygen can be prepared by reacting the appropriate diphenol of structure 5 with two equivalents of an appropriately substituted chloroformate (R$_1$OCOCR) in a previously dried basic organic solvent such as pyridine, at room temperature to provide the desired dicarbonate as defined by structure 6.

The compounds of Formula I wherein Y is sulfur and Z is NH can be prepared by reacting the appropriate diphenol of structure 5 with two equivalents of an appropriately substituted isothiocyanate (R$_1$NCS) in a wet solvent such as 50% aqueous pyridine, with minimal heating to provide the compound as defined by structure 6.

The compounds of Formula I wherein Y is sulfur and Z is sulfur can be prepared by reacting the appropriate diphenol of structure 5 with two equivalents of an appropriately substituted chlorodithioformate (R$_1$SCSCl) in a dry basic organic solvent such as pyridine, at room temperature to provide the compound as defined by structure 6.

The compounds of Formula I wherein Y is sulfur and Z is oxygen can be prepared by reacting the appropriate diphenol of structure 5 with two equivalents of an appropriately substituted chlorothionoformate (R$_1$OCSCl) in a dry basic organic solvent such as pyridine, at room temperature to provide the compound as defined by structure 6.

The compounds of Formula I wherein Y is oxygen and Z is sulfur can be prepared by reacting the appropriate diphenol of structure 5 with two equivalents of an appropriately substituted chlorothiolformate (R$_1$SCOCl) in a dry basic organic solvent such as pyridine, at room temperature to provide the compound as defined by structure 6.

Scheme IV

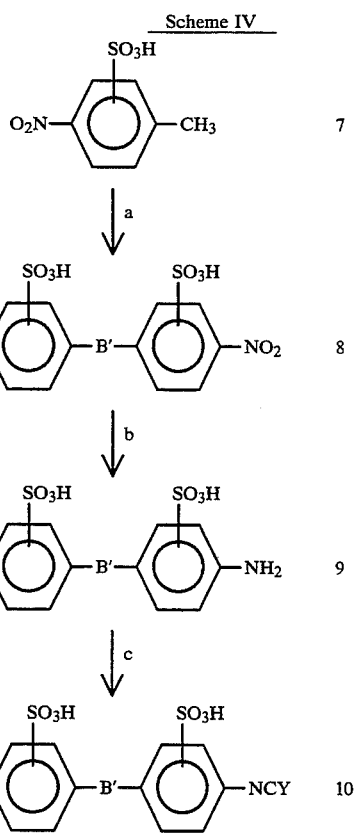

B' = CH$_2$CH$_2$ or CH=CH

Starting materials for use in the general synthetic procedures outlined in Schemes I through III are readily available to one of ordinary skill in the art. As described in Scheme IV, step a, the appropriately substituted p-nitrotoluenesulfonic acid (GB 1,164,752 Sep. 24, 1969) can be dimerized by treatment with sodium hypochlorite and sodium hydroxide in a protic solvent such as diethylene glycol to yield the appropriately substituted dinitro compound of structure 8. In step b, compound 8 can be treated with hydrazine hydrate and an alkali such as potassium hydroxide in a protic solvent such as diethylene glycol under reflux to yield the appropriately substituted diamino comound of structure 9 with B'=CH=CH. In step b, compound 8 can also be treated with hydrazine hydrate in the absence of an alkali in a protic solvent such as diethylene glycol under reflux to yield the appropriately substituted diamino compound of structure 9 with B'=CH$_2$CH$_2$(Huang-Minlon, *J.Am. Chem. Soc.* (1948) 70, 2802). Treatment of the appropriate diamino compound of structure 9 with thiophosgene or phosgene in water with an alkali such as sodium hydroxide added will yield the appropriately substituted compound of structure 10 with Y=sulfur or oxygen respectively (Ship, S. et al. *J. Mebrane Biol.* (1977) 33, 311).

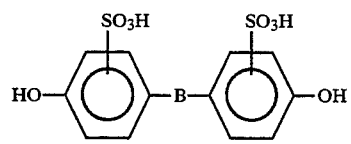

The 4,4'-dihydroxy compound of structure 11 can be prepared by reacting the appropriately substituted compound of structure 9 with an alkali such as sodium hydroxide in water at reflux.

Applicants prefer those compounds of formula I wherein B is a —CH$_2$—CH$_2$ group and more prefer those wherein B is a —CH=CH— group, especially those of the trans configuration. Applicants also prefer those compounds of formula I wherein X and Z are each an NH and wherein Y is an oxygen or more preferably a sulfur. Also preferred are those formula I compounds wherein R$_1$ is a m-phenylsulfonate or p-phenylsulfonate group. Applicants further prefer those compounds of formula I wherein M$_1$, M$_2$, and M$_3$, if present, are each independently a hydrogen or a sodium cation.

The preferred compounds of this invention are 2,2'-(1,2-ethenediyl)bis[5-[[(4-sulfophenyl)amino]thioxomethyl]amino]benzenesulfonic acid, tetrasodium salt;

2,2'-(1,2-ethenediyl)bis[5-[[(3-sulfophenyl)amino]thioxomethyl]amino]benzenesulfonic acid, tetrasodium salt;

2,2'-(1,2-ethenediyl)bis[5-[[(4-sulfophenyl)amino]thioxomethyl]amino]benzenesulfonic acid, tetrasodium salt;

2,2'-(1,2-ethenediyl)bis[5-[[(3-sulfophenyl)amino]thioxomethyl]amino]benzenesulfonic acid, tetrasodium salt;

2,2'-(1,2-ethenediyl)bis[5-[methylcarbonyl]amino]benzenesulfonic acid, disodium salt;

2,2'-(1,2-ethanediyl)bis[5-[[(4-methyphenyl)amino]thioxomethyl]amino]benzenesulfonic acid, disodium salt; and 2,2'-(1,2-ethenediyl)bis[5-[[(4-methylphenyl)amino]thioxomethyl]amino]benzenesulfonic acid, disodium salt.

The sulfonated stilbenes can be used to prevent infection of cells with HIV and syncytium formation in cells with established HIV infections, or against other related viruses having gp120 surface protein as well the Herpes Simplex Viruses (HSV) I and II and the cytomegalovirus (CMV). The sulfonated stilbenes can be used to treat AIDS and ARC and other diseases caused by the retrovirus HIV or other related viruses having gp120 surface protein as well as diseases caused by the Herpes Simplex Viruses (HSV) I and II and cytomegalovirus (CMV).

The amount of sulfonated stilbene of formula 1 which is needed to prevent syncytium formation in HIV, HSV or CMV infected cells can be any effective amount. Experimentally, applicants have determined that sulfonated stilbenes when employed at a concentration of 50–100 μg/ml resulted in complete inhibition of syncytium formation as well as reduced the presence of P24 antigen, an indicator of HIV viral replication. The amount of sulfonated stilbene of formula I to be administered in order to treat AIDS or ARC or other disease caused by HIV infection as well as diseases caused by HSV and CMV infection can vary widely according to the particular dosage unit employed, the period of treatment, the age and sex of the patient treated, the nature and extent of the disorder treated, and other factors well-known to those practicing the appropriate arts. Moreover, sulfonated stilbenes of formula I can be used in conjunction with other agents known to be useful in the treatment of retroviral diseases and agents known to be useful to treat the symptoms of and complications associated with diseases and conditions caused by retroviruses. The anti-virally effective amount of sulfonic acid stilbenes of formula I to be administered will generally range from about 15 mg/kg to 500 mg/kg. A unit dosage may contain from 25 to 500 mg of the sulfonic acid stilbenes, and can be taken one or more times per day. The sulfonated stilbenes of formula I can be administered with a pharmaceutical carrier using conventional dosage unit forms either orally or parenterally.

For oral administration sulfonated stilbenes of formula I can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The sulfonated stilbenes of formula I may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4methanol, ethers such as poly(ethylene glycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the sulfonated stilbene in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The phrmaceutically effective compound dissolves in and diffuses through the matrix itself. Release by microporous flow occurs when the pharmaceutically effective compound is transported through a liquid phase in the pores of the matrix.

The following examples present typical syntheses as described in Schemes I through III. These examples are understood to be illustrative only and are not intended to limit the scope of the present invention in any way. As used herein, the following terms have the indicated meanings: "g" refers to grams; "mg" refers to milligrams; "mmol" refers to millimoles; "mL" refers to milliliters; "°C" refers to degrees Celsius; "μM" refers to micromolar; "nM" refers to nanomolar.

EXAMPLE 1

Preparation of 2,2'-(1,2-ethenediyl)bis[5-[[(4-sulfophenyl)amino]thioxomethyl]amino]benzenesulfonic acid, tetrasodium salt

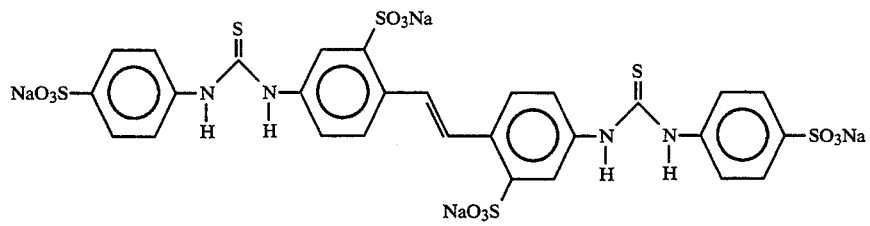

Combine sulfanilic acid (84 mg, 0.43 mmol) and 4,4'-diiisothiocyanato-2,2'-stilbenedisulfonic acid, disodium salt (106 mg, 0.21 mmol) with a mixture of water (1.5 mL) and pyridine (1.5 mL). Stir for 24 hours. Filter the reaction and concentrate under vacuum. Dry the product under high vacuum at 90° C. for 20 hours to yield the title compound (104 mg, 52%) as a rust colored solid:

Anal. Calcd for ($C_{28}H_{32}N_4Na_2O_{18}S_6$): C, 33.74;H, 3.24;N, 5.62;Found: C, 33.68;H, 3.46;N, 5.66.

EXAMPLE 2

Preparation of 3,3'-(1,2-ethenediyl)bis[6-[[(4-sulfophenyl)amino]thioxomethyl]amino]benzenesulfonic acid, tetrasodium salt

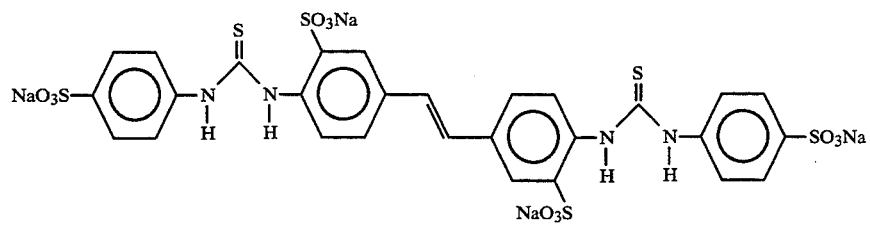

Preparation of
4,4'-diisothiocyanato-3,3'-stilbenedisulfonic acid,
disodium salt, Scheme IV, step a;

Combine p-nitrotoluene-m-sulfonic acid (5 g, 27 mmol) and diethylene glycol (30 mL) and warm to 40°–45° C. Add slowly to this with stirring, a mixture of sodium hypochlorite (5% available chlorine, 50 mL) and a solution of sodium hydroxide (6 g in 8 mL water). After addition, maintain the temperature at 50°–55° C. and stir for 35 minutes. Cool the reaction and filter to yield 4,4'-dinitrostilbene-3,3'-disulfonic acid, disodium salt. Convert this to the diacid by treatment with 1M hydrochloric acid, filter and concentrate under vacuum to yield 4,4'-dinitrostilbene-3,3'-disulfonic acid.

Scheme IV, step b

Combine 4,4'-dinitrostilbene-3,3'-disulfonic acid (1 g, 2.32 mmol) with diethylene glycol (40 mL), hydrazine hydrate (2.5 mL, 80 mmol) and potassium hydroxide (2 g) and reflux for 30 minutes. Remove the condenser and allow the reaction to concentrate through evaporation. Allow the reaction temperature to rise to approximately 200° C. Reflux at this temperature for one to three hours until the reaction changes from a dark colored solution to nearly colorless or light brown. Cool the reaction, dilute with water (20 mL) and acidify with concentrated hydrochloric acid. Filter the reaction and rinse the precipitate with cold water (5 mL). Collect the precipitate and dissolve in water (10 mL) with 2 eq of sodium bicarbonate. Filter the solution and concentrate under vacuum to yield 4,4'-diaminostilbene-3,3'-disulfonic acid, disodium salt.

Scheme IV, step c

Dissolve the 4,4'-diaminostilbene-3,3'-disulfonic acid, disodium salt (41 mg, 0.1 mmol) in 0.1% sodium chloride (2 mL). Treat this solution with thiophosgene (0.5 mL) at room temperature with vigorous stirring for 30 minutes. Remove the excess thiophosgene by repeated extraction with ether. Filter the aqueous layer and rinse the precipitate with cold 0.01N HCl (0.5 mL) and cold water (0.5 mL). Dissolve the precipitate in water (2 mL) with 2 eq of sodium bicarbonate, filter and concentrate under vacuum to yield 4,4'-diiisothiocyanato-3,3'-stilbenedisulfonic acid, disodium salt.

Combine sulfanilic acid (78 mg, 0.40 mmol) and 4,4'-diiisothiocyanato-3,3'-stilbenedisulfonic acid, disodium salt (100 mg, 0.20 mmol) with a mixture of water (1.5 mL) and pyridine (1.5 mL). Stir for 24 hours. Filter the reaction and concentrate under vacuum to yield the title compound.

EXAMPLE 3

Preparation of 2,2'-(1,2-ethenediyl)bis[5-[[(3-sulfophenyl)amino]thioxomethyl]amino]benzenesulfonic acid, tetrasodium salt

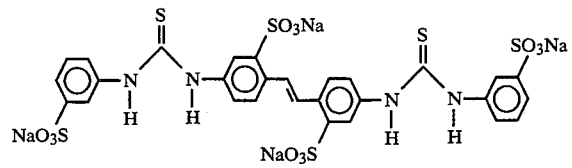

Combine metanilic acid (73 mg, 0.42 mmol) with sodium bicarbonate (35 mg, 0.42 mmol) in water (1.5 mL). To this solution add 4,4'-diisothiocyanato-2,2'-stilbenedisulfonic acid, disodium salt (104 mg, 0.21 mmol), followed by pyridine (1.5 mL). Stir the reaction for 24 hours, filter and concentrate under vacuum. Dry the product under vacuum at 90° C. for 20 hours to yield the title compound (108 mg, 58%) as a light brown solid.

EXAMPLE 4

Preparation of 2,2'-(1,2-ethanediyl)bis[5-[[(4-sulfophenyl)amino]thioxomethyl]amino]benzenesulfonic acid, tetrasodium salt

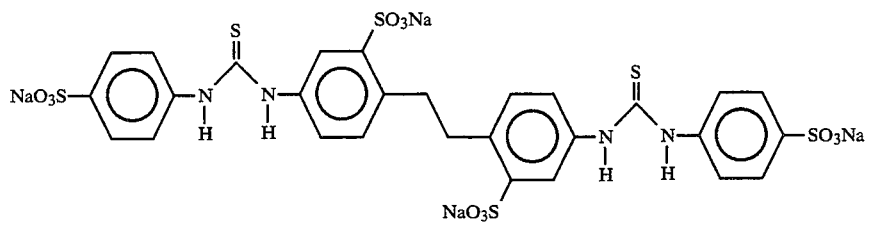

Combine 4,4'-diisothiocyanato-2,2'-dihydrostilbenedisulfonic acid disodium salt (205 mg, 0.41 mmol) and sulfanilic acid sodium salt (160 mg, 0.82 mmol) with a mixture of water (5 mL) and pyridine (5 mL). Stir the reaction for 72 hours, filter and concentrate under high vacuum. Recrystallize the residue from 20% diethyl ether/methanol. Dry the solid at 70° C. under vacuum to yield the title compound (115 mg, 32%).

EXAMPLE 5

Preparation of 3,3'-(1,2-ethanediyl)bis[6-[[(4-sulfophenyl)amino]thioxomethyl]amino]benzenesulfonic acid, tetrasodium salt

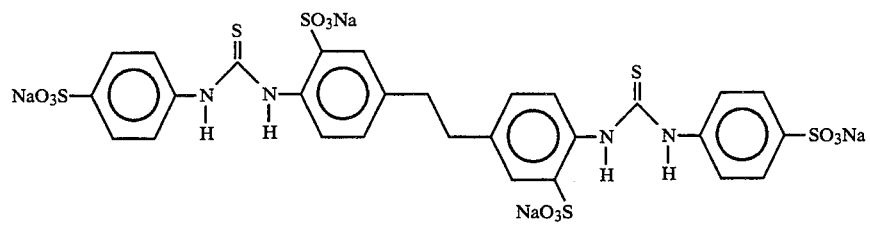

Preparation of
4,4'-diisothiocyanato-3,3'-dihydrostilbenesulfonic acid,
disodium salt, Scheme IV, step b Combine 4,4'-diaminostilbene-3,3'-disulfonic acid (1 g, 2.7 mmol) as described in example 2, with diethylene glycol and hydrazine hydrate (4 mL, 128 mmol). Reflux the reaction for 30 minutes. Remove the condenser and allow the reaction to concentrate through evaporation. The reaction temperature rises to approximately 200° C. Reflux at this temperature for one to three hours until the reaction changes from a dark colored solution to nearly colorless or light brown. Cool the reaction, dilute with water (20 mL) and acidify with concentrated hydrochloric acid. Filter the reaction and rinse the precipitate with cold water (5 mL). Collect the precipitate and dissolve in water (10 mL) with 2 eq of sodium bicarbonate. Filter the solution and concentrate under vacuum to yield 4,4'-diaminodihydrostilbene-3,3'-disulfonic acid, disodium salt.

Scheme IV, step c

Dissolve the 4,4'-diaminodihydrostilbene-3,3'-disulfonic acid, disodium salt (42 mg, 0.1 mmol) in 0.1% sodium chloride (2 mL). Treat this solution with thiophosgene 0.5 mL) at room temperature with vigorous stirring for 30 minutes. Remove the excess thiophosgene by repeated extraction with ether. Filter the aqueous layer and rinse the precipitate with cold 0.01N HCl (0.5 mL) and cold water (0.5 mL). Dissolve the precipitate in water (2 mL) with 2 eq of sodium bicarbonate, filter and concentrate under vacuum to yield 4,4'-diiisothiocyanato-3,3'-dihydrostilbenedisulfonic acid, disodium salt.

Combine sulfanilic acid (78 mg, 0.40 mmol) and 4,4'-diiisothiocyanato-3,3'-dihydrostilbenedisulfonic acid, disodium salt (100 mg, 0.20 mmol) with a mixture of water (1.5 mL) and pyridine (1.5 mL). Stir for 24 hours. Filter the reaction and concentrate under vacuum to yield the title compound.

EXAMPLE 6

Preparation of
2,2'-(1,2-ethanediyl)bis[5-[[(3-sulfophenyl)amino]thioxomethyl]amino]benzenesulfonic acid, tetrasodium salt

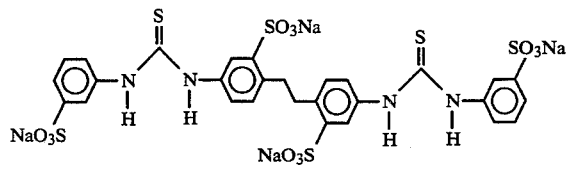

Combine 4,4'-diisothiocyanato-2,2'-dihydrostilbenedisulfonic acid, disodium salt (213 mg, 0.43 mmol) and metanilic acid (147 mg, 0.85 mmol) with sodium bicarbonate (72 mg, 0.85 mmol) in a mixture of water (6 mL) and pyridine (6 mL). Stir the reaction for 72 hours and concentrate under vacuum. Dissolve the residue in methanol 30 mL and filter. Concentrate the filtrate under vacuum and recrystallize the residue from 30% ethanol/diethyl ether to yield after drying under vacuum at 70° C. to yield the title compound (133 mg, 35%).

EXAMPLE 7

Preparation of
2,2'-(1,2-ethenediyl)bis[5-[(1,1-dimethylethoxy)carbonyl]amino]benzenesulfonic acid, disodium salt

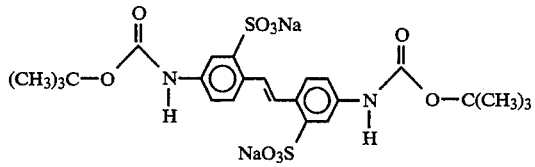

Dissolve 4,4'-diamino-2,2'-stilbenedisulfonic acid (100 mg, .27 mmol) in 50% aqueous dioxane (3 mL). Add triethylamine (0.11 mL, 0.81 mmol) and 2-(tert-butoxycarbonyloxyimino)-2-phenylacetonitrile (145 mg, 0.59 mmol). Stir the reaction for 4 hours at room temperature. Add water (30 mL) and rinse with diethyl ether (2×30 mL). Add sodium bicarbonate (43 mg, 0.54 mmol), filter the solution and concentrate under high vacuum to yield the title compound.

EXAMPLE 8

Preparation of 2,2'-(1,2-ethenediyl)bis[5-[[(phenylmethyl)thio]thioxomethyl]amino]benzenesulfonic acid, disodium salt

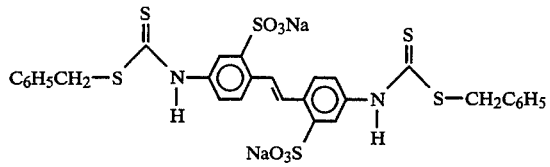

Dissolve 4,4'-diisothiocyanostilbene-2,2'disulfonic acid, disodium salt (100 mg, 0.20 mmol) in a mixture of water (5 mL) and pyridine (5 mL). Add benzyl mercaptan (0.05 mL, 0.40 mmol) and stir for 24 hours at room temperature. Filter the reaction and concentrate under high vacuum to yield the title compound.

EXAMPLE 9

Preparation of
2,2'-(1,2-ethenediyl)bis[5-[methylcarbonyl]amino]benzenesulfonic acid, disodium salt

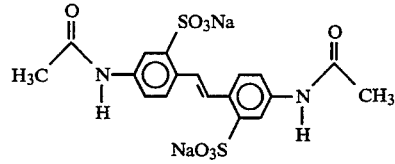

Dissolve 4,4'-diamino-2,2'-stilbenedisulfonic acid, disodium salt (1.04 g, 2.81 mmol) in water (20 mL) and treat with sodium bicarbonate (0.47 g, 5.62 mmol) with stirring. Remove the solvent under high vacuum. Add acetic anhydride (150 mL) to the residue and reflux for 16 hours. Cool the reaction, and suction filter to collect the precipitate. Suspend the precipitate in diethyl ether (200 mL) and suction filter. Repeat the rinsing process one time. Collect the precipitate and dry under vacuum at 70° C. for 48 hours to yield the title compound (1.05 g, 75%) as a light tan powder.

EXAMPLE 10

Preparation of
4,4'-[1,2-ethenediylbis[(3-sulfo-4,1-phenylene)iminocarbonothioylimiino]]bis-1-naphthalenesulfonic acid, tetrasodium salt

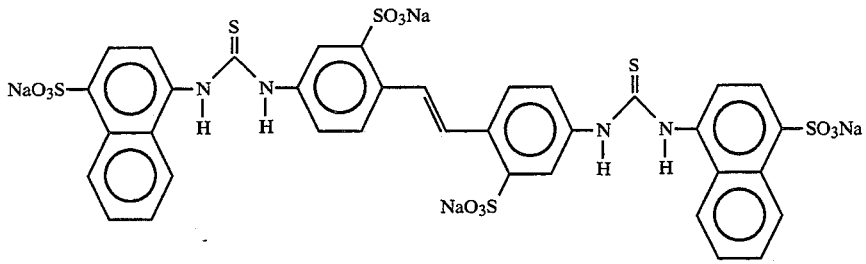

Dissolve 4,4'-diisothiocyanostilbene-2,2'-disulfonic acid, disodium salt (100 mg, 0.20 mmol) in a mixture of water (5 mL) and pyridine (5 mL). Add 4-amino-1-naphthalenesulfonic acid, sodium salt (98 mg, 0.40 mmol) and stir for 24 hours at room temperature. Filter the reaction and concentrate under high vacuum to yield the title compound.

EXAMPLE 11

Preparation of
2,2'-(1,2-ethenediyl)bis[5-[(phenylamino)carbonyl]oxy]-benzenesulfonic acid, disodium salt

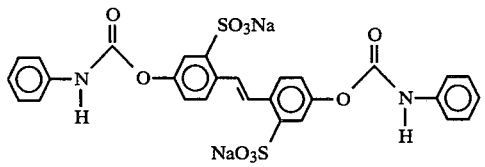

Disslove 4,4'-diamino-2,2'-stilbenedisulfonic acid, disodium salt (4 g, 9.66 mmol) in water (50 mL). Add sodium hydroxide (4 g, 100 mmol) and heat the reaction to reflux for 30 hours. After cooling the reaction acidify with 1M HCl and extract with ethyl acetate (5×50 mL). Combine the organic extracts, dry over sodium sulfate, filter and concentrate under vacuum. Treat the residue with sodium bicarbonate (2 eq) in water (50 mL). Filter the solution and concentrate under vacuum to yield 4,4'-dihydroxy-2,2'-stilbenedisulfonic acid, disodium salt.

Combine 4,4'-dihydroxy-2,2'-stilbenedisulfonic acid, disodium salt (100 mg, 0.24 mmol) and phenyl isocyanate (0.05 mL, 0.48 mmol) in dry pyridine (3 mL). Stir for 24 hours. Filter the reaction and concentrate under high vacuum to yield the title compound.

EXAMPLE 12

Preparation of 2,2'-(1,2-ethenediyl)bis[5-(phenylamino)thioxomethoxyl]-benzenesulfonic acid, disodium salt

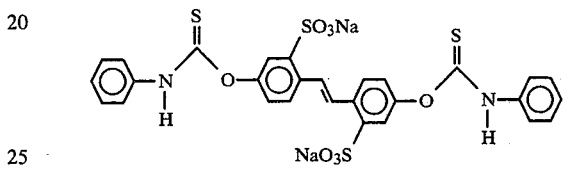

Combine 4,4'-dihydroxy-2,2'-stilbenedisulfonic acid, disodium salt (100 mg, 0.24 mmol) with phenyl isothiocyanate (0.06 mL, 0.48 mmol) in dry pyridine (3 mL). Stir for 24 hours. Filter the reaction and concentrate under high vacuum to yield the title compound.

EXAMPLE 13

Preparation of
2,2'-(1,2-ethenediyl)bis[5-[(phenylmethoxy)carbonyl]oxy]benzenesulfonic acid, disodium salt

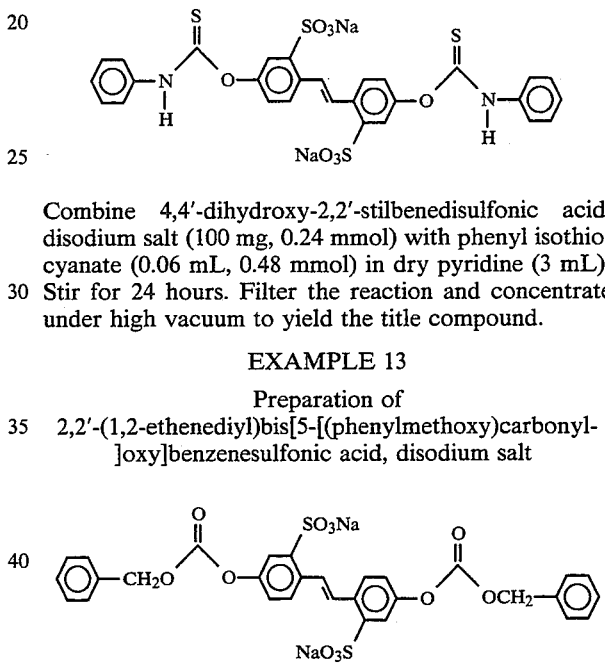

Combine 4,4'-dihydroxy-2,2'-stilbenedisulfonic acid, disodium salt (100 mg, 0.24 mmol) with benzyl chloroformate (0.07 mL, 0.48 mmol) in dry pyridine (3 mL) at room temperature. Stir the reaction for 48 hours. Filter the reation and concentrate under high vacuum to yield the title compound.

EXAMPLE 14

Preparation of
1,2-ethenediylbis(3-sulfo-4,1-phenylene)benzeneacetic acid, disodium salt

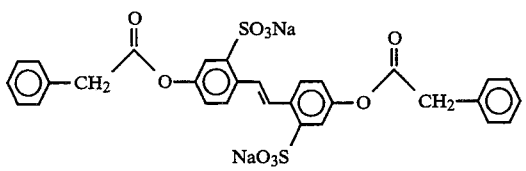

Combine 4,4'-dihydroxy-2,2'-stilbenedisulfonic acid, disodium salt (100 mg, 0.24 mmol) with phenylacetyl chloride (0.06 mL, 0.48 mmol) in dry pyridine (3 mL) at room temperture. Stir for 24 hours. Filter the reaction and concentrate under high vacuum to yield the title compound.

EXAMPLE 15

Preparation of 2,2'-(1,2-ethenediyl)bis[5-[(phenylamino)carbonyl]amino]benzenesulfonic acid, disodium salt

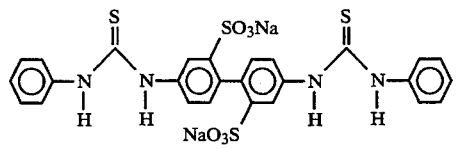

Dissolve 4,4'-diamino-2,2'-stilbenedisulfonic acid (100 mg, 0.27 mmol) in dry pyridine (3 mL). Add phenyl isocyanate (0.06 mL, 0.54 mmol) and stir for 24 hours at room temperature. Filter the reaction and concentrate under high vacuum to yield the title compound.

EXAMPLE 16

Preparation of 4,4'-bis[[(phenylamino)thioxomethyl]amino]-[1,1'-biphenyl) -2,2'-disulfonic acid, disodium salt

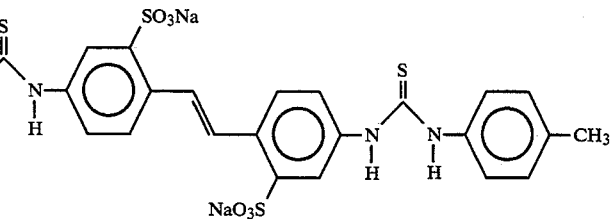

Combine 4,4'-diamino-2,2'-biphenyl disulfonic acid, disodium salt (100 mg, 0.26 mmol) with phenyl isothiocyanate (0.06 mL, 0.52 mmol) in a mixture of water (3 mL) and pyridine (3 mL). Stir for 24 hours at room temperature. Filter the reaction and concentrate under high vacuum to yield the title compound.

EXAMPLE 17

Preparation of 2,2'-(1,2-ethanediyl)bis[5-[[(4-methylphenyl)amino]thioxomethyl]amino]benzenesulfonic acid, disodium salt

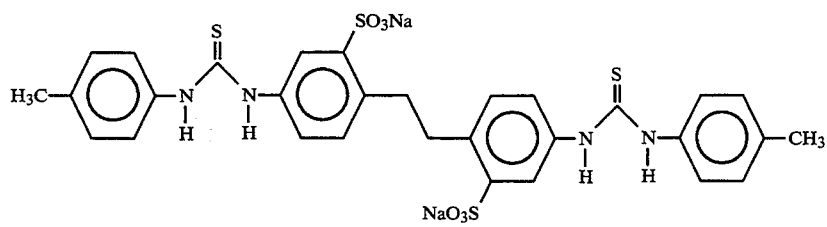

Dissolve 4,4'-diisothiocyanodihydrostilbene-2,2'-disulfonic acid, disodium salt (183 mg, 0.37 mmol) in water (10 mL). Add tetrahydrofuran (5 mL) followed by p-toluidine (153 mg, 1.46 mmol) and heat to 80° C. for 3 hours with stirring under nitrogen. Cool the reaction and rinse with toluene (4×25 mL). Concentrate the aqueous under vacuum to yield the title compound (189 mg, 71%).

EXAMPLE 18

Preparation of 2,2'-(1,2-ethenediyl)bis[5-[[(4-methylphenyl)amino]thioxomethyl]amino]benzenesulfonic acid, disodium salt

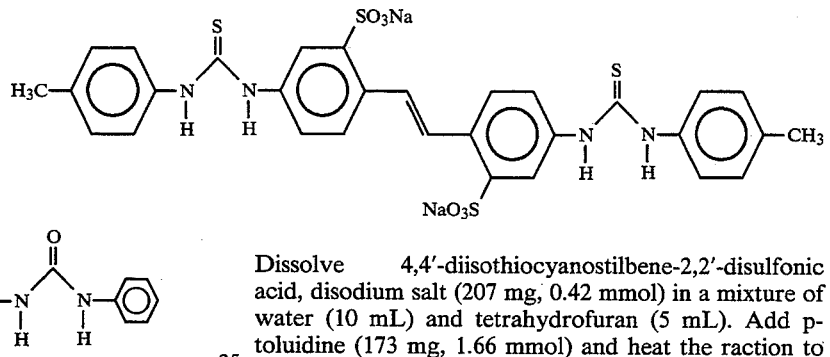

Dissolve 4,4'-diisothiocyanostilbene-2,2'-disulfonic acid, disodium salt (207 mg, 0.42 mmol) in a mixture of water (10 mL) and tetrahydrofuran (5 mL). Add p-toluidine (173 mg, 1.66 mmol) and heat the raction to 80° C. for two hours with stirring. Cool the reaction and rinse with toluene (3×25 mL) and diethyl ether (25 mL). Concentrate the aqueous phase under vacuum to yield the title compound (106 mg, 35%).

EXAMPLE 19

Preparation of 2,2'-(1,2-ethenediyl)bis[5-[[(phenylmethyl)thio]carbonyl]amino]benzenesulfonic acid, disodium salt

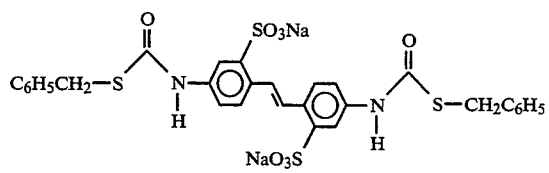

Dissolve 4,4'-diisocyanostilbene-2,2'-disulfonic acid, disodium salt (100 mg, 0.21 mmol) in anhydrous pyridine (3 mL) and add benzyl mercaptan (0.05 mL, 0.42 mmol). Stir for 24 hours. Filter the reaction and concentrate under vacuum to yield the title compound.

EXAMPLE 20

Preparation of
2,2'-(1,2-ethenediyl)bis[5-(1-thioxopentyl)amino]benzenesulfonic acid, disodium salt

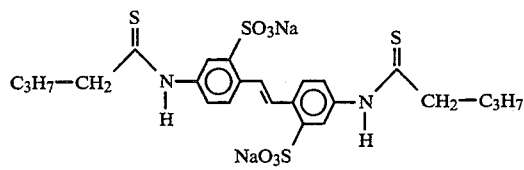

Dissolve 4,4'-diisothiocyanostilbene-2,2'-disulfonic acid, disodium salt (100 mg, 0.20 mmol) in anhydrous pyridine (3 mL) and cool to −20° C. with stirring under an atmosphere of nitrogen. Add via syringe n-butyllithium (0.25 mL of a 1.6M solution in hexane, 0.04 mmol). After 1 hour add 1M HCl (10ML) and extract with ethyl acetate (5×25 Ml). Dry the combined organic extracts over anhydrous magnesium sulfate, filter and concentrate under vacuum. Add water (3 mL) to the residue and treat with sodium bicarbonate (33 mg, 0.40 mmol). Filter the solution and concentrate under vacuum to yield the title compound.

EXAMPLE 21

Preparation of
2,2'-(1,2-ethenediyl)bis[5-[(phenylthio)thioxomethoxy]-benzenesulfonic acid, disodium salt

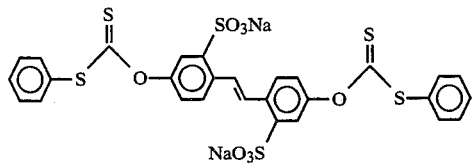

Combine 4,4'-dihydroxy-2,2'-stilbenedisulfonic acid, disodium salt (100 mg, 0.24 mmol) with phenyl chlorodithioformate (90 mg, 0.48 mmol) in dry pyridine (3 mL) at room temperture. Stir for 24 hours. Filter the reaction and concentrate under high vacuum to yield the title compound.

EXAMPLE 22

Preparation of
2,2'-(1,2-ethenediyl)bis[5-[(phenylthio)carbonyl]oxy]-benzenesulfonic acid, disodium salt

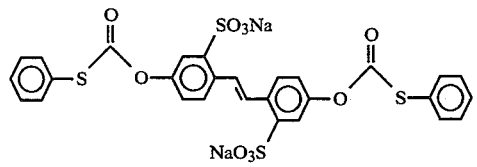

Combine 4,4'-dihydroxy-2,2'-stilbenedisulfonic acid, disodium salt (100 mg, 0.24 mmol) with phenyl chlorothiolformate (83 mg, 0.48 mmol) in dry pyridine (3 mL) at room temperture. Stir for 24 hours. Filter the reaction and concentrate under high vacuum to yield the title compound.

EXAMPLE 23

Preparation of
2,2'-(1,2-ethenediyl)bis[5-(phenoxythioxomethoxy)benzenesulfonic acid, disodium salt

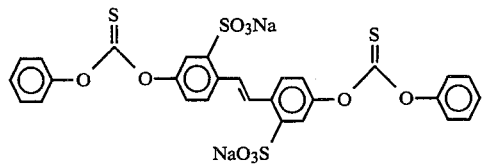

Combine 4,4'-dihydroxy-2,2'-stilbenedisulfonic acid, disodium salt (100 mg, 0.24 mmol) with phenyl chlorothionoformate (0.07 mL, 0.48 mmol) in dry pyridine (3 mL) at room temperture. Stir for 24 hours. Filter the reaction and concentrate under high vacuum to yield the title compound.

What is claimed is:

1. A compound of the formula wherein

B is —CH=CH— (cis or trans), $CH_2CH_2$ or a bond;
X is NH or oxygen;
Y is sulfur;
Z is NH, $CH_2$, oxygen or sulfur;

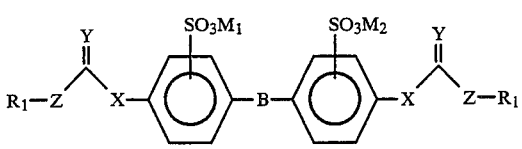

$R_1$ is $C_1$—$C_4$ alkyl, —$CH_2$—Ar, or —Ar wherein Ar is a phenyl group optionally substituted by a $C_1$-$C_4$ alkyl or $SO_3M_3$ group; and $M_1$, $M_2$, and $M_3$ are each independently a hydrogen or a pharmaceutically acceptable cation.

2. A compound of claim 1 wherein B is a —C=C— group.

3. A compound of claim 1 wherein X and Z are each independently an NH and Y is a sulfur.

4. A compound of claim 1 wherein each $R_1$ is a m-phenylsulfonate or p-phenylsulfonate.

5. A compound of claim 1 wherein $M_1$ and $M_2$ are each independently a hydrogen or a sodium cation.

6. A compound method claim 1 wherein the compound is 2,2'-(1,2-ethenediyl)bis[5-[[(4-sulfophenyl)amino]thioxomethyl]amino]benzenesulfonic acid, tetrasodium salt.

7. A compound of claim 1 wherein the compound is 2,2'-(1,2-ethenediyl)bis[6-[[(4-sulfophenyl)amino]thioxomethyl]amino]benzenesulfonic acid, tetrasodium salt.

8. A compound of claim 1 wherein the compound is 2,2'-(1,2-ethenediyl)bis[5-[[(3-sulfophenyl)amino]thioxomethyl]amino]benzenesulfonic acid, tetrasodium salt.

9. A compound of claim 1 wherein the compound is 2,2'-(1,2-ethanediyl)bis[5-[[(4-sulfophenyl)amino]thioxomethyl]amino]benzenesulfonic acid, tetrasodium salt.

10. A compound of claim 1 wherein the compound is 2,2'-(1,2-ethanediyl)bis[5-[[(4-methylphenyl)amino]thioxomethyl]amino]benzenesulfonic acid, disodium salt.

11. A compound of claim 1 wherein the compound is 2,2'-(1,2-ethenediyl)bis[5-[[(4-methylphenyl)amino]thioxomethyl]amino]benzenesulfonic acid, disodium salt.

* * * * *